United States Patent [19]

Fleet et al.

[11] Patent Number: 5,153,325
[45] Date of Patent: Oct. 6, 1992

[54] FUCOSIDASE INHIBITOR

[75] Inventors: George W. J. Fleet; Sung K. Namgoong, both of Oxford, United Kingdom

[73] Assignee: Monsanto Company, St. Louis, Mo.

[21] Appl. No.: 855,464

[22] Filed: Mar. 20, 1992

Related U.S. Application Data

[60] Continuation of Ser. No. 600,950, Oct. 22, 1990, abandoned, which is a division of Ser. No. 372,415, Jun. 27, 1989, Pat. No. 4,849,430.

[51] Int. Cl.$^5$ ............................................. C07D 211/36
[52] U.S. Cl. ................................................... 546/242
[58] Field of Search ........................................ 546/242

[56] References Cited

PUBLICATIONS

Fleet et al., FEBS Lett. 237, 128–132 (1988).
Karpas et al., Proc. Natl. Acad. Sci. USA 85, 9229–9233 (1988).
Liu et al., J. Org. Chem. 52, 4717–4721 (1987).
Rhinehart et al., J. Pharmacol. Exptl. Therap. 241, 915–920 (1987).
Kite et al., Tetrahedron Lett. 29, 6483–6486 (1988).
Fleet et al., J. Chem. Soc. Chem. Commun. 1985, 841–842, 1988, 483–485.
Fleet et al., J. Chem. Sco. Perkins Trans. 1, 665–666 (1989).

*Primary Examiner*—Alan Siegel
*Attorney, Agent, or Firm*—Scott J. Meyer

[57] ABSTRACT

The synthesis of the novel fucosidase inhibitor, 2,6-imino-2,6,7-trideoxy-D-glycero-D-gluco heptitol, is disclosed.

2 Claims, No Drawings

FUCOSIDASE INHIBITOR

This is a continuation of application Ser. No. 07/600,950, filed on Oct. 22, 1990, now abandoned, which is a division of application Ser. No. 07/372,415, filed Jun. 27, 1989, now U.S. Pat. No. 4,849,430.

BACKGROUND OF THE INVENTION

This invention relates to a novel fucosidase inhibitor. More particularly, the invention relates to the synthesis of the novel iminoheptitol, 2,6-imino-2,6,7-trideoxy-D-glycero-D-gluco heptitol.

The α-glucosidase inhibitor deoxynojirimycin (1) [Walker et al., *Proc. Natl. Acad. Sci. USA* 84, 8120 (1987); Tyms et al, *Lancet* 1987 1026; Gruters et al., *Nature* 330, 74 (1987)] and its alkylated derivatives [Fleet et al., *FEBS Lett.* 237, 128–132 (1988); Karpas et al., *Proc. Natl. Acad. Sci. USA* 85, 9229–9233 (1988)] inhibit human immunodeficiency virus synctium formation and virus replication and may have potential as antiretroviral agents [Sunkara et al., *Biochem. Biophys. Res. Commun.* 148, 206 (1987)]. See also copending applications Ser. No. 07/248,461, filed Sep. 23, 1988 and Ser. No. 07/249,144, filed Sep. 26, 1988, now U.S. Pat. No. 4,999,360.

The β-D-glucopyranosyl derivative (3) of α-homonojirimycin (2) was first designed as a synthetic transition state inhibitor of α-glucosidases [Liu et al., *J. Org. Chem.* 52, 4717 (1987)] and is in clinical trials in relation to the treatment of diabetes mellitus [Rhinehart et al., *J. Pharmacol. Expt'l. Therapeut.* 241, 915 (1987)]. α-Homonojirimycin, the first example of a naturally occurring azapyranose analogue of a heptose, has recently been isolated from *Omphalea diandra L.* and has been demonstrated to be a potent inhibitor of digestive α-glucosidase activity [Kite et al., *Tetrahedron Lett.* 29, 6483 (1988)]. These azaheptoses provide the opportunity for the synthesis of a class of stable aza-disaccharides such as (3) which may confer additional potency and/or specificity in comparison with the corresponding azapyranose analogues such as deoxynojirimycin. 1,5-Dideoxy-1,5-imino-L-fucitol, also referred to as deoxyfuconojirimycin (4), first prepared by lengthy procedures from D-glucose, [Fleet et al., *J. Chem. Soc. Chem. Commun.* 1985, 841–842; Fleet et al., *Ibid.* 1988, 483–485] is a very powerful and highly specific inhibitor of a number of mammalian'α-L-fucosidases. See also copending application Ser. No. 07/252,846, filed Oct. 3, 1988 now U.S. Pat. No. 4,910,310 for the synthesis of derivatives of deoxyfuconojirimycin having enzyme inhibitory activity.

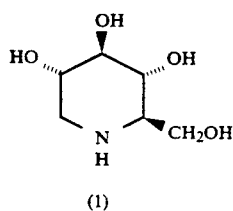

(1)

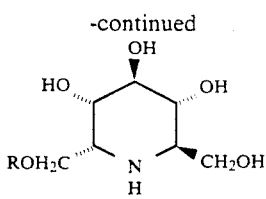

(2) R = H
(3) R = β-D-glucopyranosyl

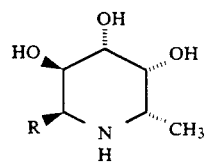

(4) R = H
(5) R = CH₂OH

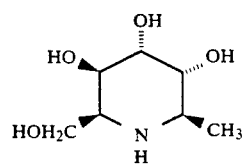

(6)

BRIEF DESCRIPTION OF THE INVENTION

In accordance with the present invention, the novel fucosidase inhibitor, 2,6-imino-2,6,7-trideoxy-D-glycero-D-gluco-heptitol (6), is synthesized in the free base form or in the acid salt form, e.g. HCl. An attempted synthesis of α-L-homofuconojirimycin (5) from diacetone mannose surprisingly resulted, instead, in the preparation of the foregoing epimeric iminoheptitol (6). In this synthesis, the catalytic hydrogenation of 6-azido-7-O-tert-butyldimethylsilyl-1,6-dideoxy-3,4-O-isopropylidene-L-gulo-heptul-2-ose followed by hydrolytic removal of the protecting groups resulted in the novel iminoheptitol (6). That is, the stereochemical result of catalytic hydrogenation of the C=N bond in a 3,4,5,6-tetrahydropyridine was determined by a bulky substituent at C-6, rather than by a 3,4-O-isopropylidene group. Thus, it has been shown that a suitable protected hydroxymethyl group can control the hydrogenation sterochemistry of the imine regardless of the other groups in the piperidine ring.

DETAILED DESCRIPTION OF THE INVENTION

In a short synthesis of deoxyfuconojirimycin (4) from D-lyxonolactone as reported by Fleet et al., *J. Chem. Soc. Perkins Trans.* 1, 665–666 (1989), treatment of the azidolactone (7) with methyl lithium gave the azidolactol (8); catalytic hydrogenation of (8) resulted in reduction of the azide to the corresponding amine and subsequent intramolecular cyclization to give the imine (9). Further hydrogenation gave only the protected iminofucitol (10) formed by addition of hydrogen from the least hindered side of the C=N; the stereochemistry of reduction of the imine (9) was completely determined by the adjacent isopropylidene group.

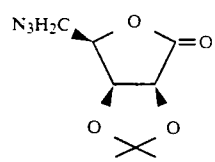

(7)

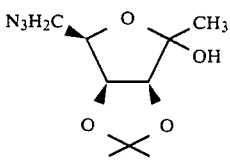

(8)

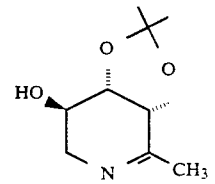

(9)

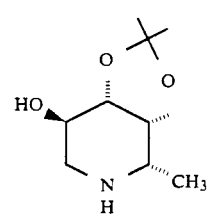

(10)

(11)

(12) R = R' = H
(13) R = [Si]; R' = H
(14) R = [Si]; R' = SO₂CF₃
    [Si] = SiMe₂t-Bu

(15)

(16)

In an attempted analogous synthesis of α-L-homofuconojirimycin (5), the epimeric iminoheptitol (6) was unexpectedly obtained, instead. Thus, diacetone mannose [Schmidt, *Meth. Carbohydr. Chem.* 2, 819 (1963)]was oxidized by pyridinium chlorochromate in the presence of molecular sieve to give the corresponding lactone (11) [Ohle and Berend, *Chem. Ber.* 58, 2590 (1925); Goodyear and Haworth, *J. Chem. Soc.* 1927, 3136] in 90% yield on a 20 g scale; other oxidations of diacetone mannose to (11) have been reported previously by Buchanan et al., *Tetrahedron* 40, 119 (1984); Horton and Jewell, *Carbohyd. Res.* 2 251 (1986). Selective hydrolysis of the side chain acetonide with aqueous acetic acid gave the diol (12) [Barker et al., Chem. Ind. 1958, 758; Heilbron's Dictionary of Organic Compounds 4, p. 3629, Chapman and Hall, 1982] [79% yield]. Reaction of (12) with tert-butylchlorodimethylsilane permitted selective protection of the primary hydroxyl group to give (13) [93% yield]; esterification of the remaining free alcohol function in (13) with trifluoromethanesulphonic anhydride gave the corresponding triflate (14) which, on subsequent treatment with azide, gave the azidolactone (15), i.e. 5-azido-6-O-tert-butyldimethylsilyl-5-deoxy-2,3-O-isopropylidene-L-gulono-1,4-lactone, in 70% yield [65% yield from (12)]. Reaction of (15) with methyl lithium in tetrahydrofuran at −78° C. gave the protected L-gulo-heptulose (16), i.e. 6-azido-7-O-tert-butyldimethylsilyl-1,6-dideoxy-3,4-isopropylidene-L -gulo-heptul-2-ose, in 82% yield as a single anomer; the stereochemistry at C-2 in (16) has not been determined.

Synthesis of analogous azidolactones, viz. 5-azido-6-O-tert-butyldimethylsilyl-5-deoxy-2, 3-O-isopropylidene-D-mannono-1,4-lactone and the epimeric L-mannonolactone, are disclosed in copending application Ser. No. 07/249,153, filed Sep. 26, 1988, now U.S. Pat. No. 4,861,891. The use of said D-mannonolactone as an intermediate to the production of novel fucosidase inhibitors is disclosed in applicants' copending application Ser. No. 07/371,943 filed Jun. 27, 1989.

The addition of alkyl lithiums to sugar lactones to give mono-adducts in good yields is a common procedure [Tam and Fraser-Reid, *J. Org. Chem.* 45, 1344 (1980); Ogura and Takahasi, Ibid. 39, 1374 (1974)] and in one case it has been established by x-ray crystallography that the product is derived from attack by the alkyl lithium from the most hindered side [Ogura et al., *Chem. Pharm. Bull.* 26, 2782 (1978)].

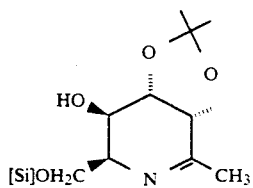

(17)

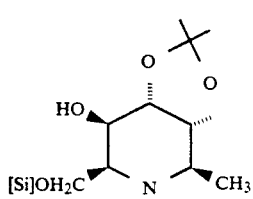

(18)

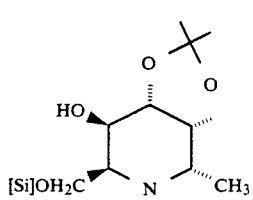

(19)

[Si] = SiMe₂t-Bu

Hydrogenation of the azidolactol (16) in ethyl acetate in the presence of platinum oxide gave a single major product (18) in 47% yield, in which the approach of hydrogen to the carbon-nitrogen double bond has been determined by the protected hydroxymethyl substituent on the piperidine ring. The imine (17), formed by reduction of the azide in (16) followed by intramolecular condensation of the amino function with the carbonyl of the ketose, would give (19) [as a precursor to α-L-homofuconojirimycin (5)] if the isopropylidene ketal function in (17) controlled the stereochemistry of the addition of hydrogenation; no compound corresponding to (19) was isolated from the reaction. The stereochemical result of the hydrogenation of the intermediate imine (17) was initially indicated by equilibrium nOe (nuclear Overhauser effect) measurements on the protected amine (18); in particular, irradiation of H-5 caused no enhancement of H-6. Also, a transdiaxial relationship between H-5 and H-6 was indicated by the coupling constants in the free base (6) [$J_{5,6}$=10.3 Hz] and in the hydrochloride of (6) [$J_{5,6}$=10.7 Hz]. An x-ray crystallographic analysis of the hydrochloride of (6) firmly established the stereochemical course of the reduction; reduction of the imine is determined solely by steric bulk, rather than by chelation of any of the oxygen functions to the heterogeneous catalyst. All attempts to isolate (19) from reductions of the azido lactol have been unsuccessful.

Although the HCl salt form of the novel iminoheptitol (6) is specifically described herein, it will be appreciated that other biologically and pharmaceutically acceptable salt forms can be substituted for the HCl with substantially equivalent results, for example, acetate, carbonate, sulfate, oxalate and the like.

The following examples will further illustrate the invention although the invention is not limited to these specific examples.

Methods

M.p.s were recorded on a Kofler block. Infra red spectra were recorded on a Perkin-Elmer 297 spectrophotometer. Optical rotations were measured on a Perkin-Elmer 241 polarimeter; concentrations are given in g/ 100 ml. ¹H NMR spectra were run at 200 MHz on a Varian Gemini spectrometer, or at 300 MHz on a Bruker WH 300 spectrometer or at 500 MHz on a Bruker AM 500 spectrometer. ¹³C NMR spectra were recorded on a Varian Gemini (50 MHz) or a Bruker AM 250 (62.9 MHz) or a Bruker AM 500 (125.0 MHz) spectrometer. For NMR spectra in D₂O, 1,4-dioxane (δ 67.6) was used as an internal standard. Mass spectra were recorded on VG Micromass ZAB 1F or MM 30F spectrometers. Microanalyses were performed by the microanalytical services of the Dyson Perrins Laboratory, Oxford, U.K. TLC was performed on aluminum pre-coated silica gel (Merck) plates, and compounds were visualized with a spray of 0.2% w/v concentrated sulphuric acid and 5% ammonium molybdate in 2N sulphuric acid. Flash chromatography was carried out using Merck Kieselgel 60, 230–400 mesh. Tetrahydrofuran was distilled from a solution dried with sodium in the presence of benzophenone under dry nitrogen. D-Mannose was obtained from Sigma Chemical Company and was converted into 2,3:5,6-di-0-isopropylidene-D-mannofuranose, m.p. 118°–121° C. (lit. m.p. 121°–122° C.), in 82% yield as previously described by Schmidt, Carbohydr. Chem. 2, 819 (1963).

EXAMPLE 1

2,3:5,6-Di-O-isopropylidene-D-mannono-1,4-lactone (11)

A solution of 2,3:5,6-di-O-isopropylidene-D-mannofuranose (diacetone mannose) (20 g, 76.9 mmol) in dichloromethane (100 ml) was added to a solution of pyridinium chlorochromate (33.2 g, 2.0 equiv) and dry powdered molecular sieve (40 g) in dichloromethane (300 ml) at 0° C. under nitrogen. The reaction mixture was stirred at room temperature for 30 min [when TLC (ether:hexane, 2:1) showed no starting material ($R_f$ 0.36) and one major product ($R_f$ 0.24)], diluted with ether (400 ml) and filtered through a silica plug. The silica plug was washed with ether and the filtrates were combined and the solvents removed to give, after recrystallization from ether, 2,3:5,6-di-O-isopropylidene-D-mannono-1,4-lactone (11), (18.0 g, 90%), m.p. 125°–126° C. [lit. m.p. 125°–125° C.; Ohle et al., Chem. Ber. 58, 2590 (1925); Goodyear and Haworth, J. Chem. Soc. 1927, 3136.].

EXAMPLE 2

2,3-O-Isopropylidene-D-mannono-1,4-lactone (12)

2,3:5,6-Di-O-isopropylidene-D-mannono-1,4-lactone (11) (9.0 g, 34.7 mmol) was stirred with 70% aqueous acetic acid (200 ml) at room temperature for 24 h when TLC (ethyl acetate:hexane, 2:1) showed no starting material ($R_f$ 0.68) and one major product ($R_f$ 0.10). The solvent was then removed and the residue coevaporated with toluene (2×100 ml) to give, after purification by flash chromatography (ethyl acetate:hexane, 3:1), the readily water soluble 2,3-O-isopropylidene-D-mannono-1,4-lactone (12), (6.0 g, 79%), m.p. 131°–132° C. [lit. m.p. 133° C.; Barker et al., Chem. Ind. 1958, 758; Heilbron's Dictionary of Organic Compounds, Vol. 4, p. 3629, Chapman and Hall, 1982].

EXAMPLE 3

6-O-tert-Butyldimethylsilyl-2,3-0-isopropylidene-D-mannono-1,4-lactone (13)

A solution of tert-butylchlorodimethylsilane (4.43 g, 1.20 equiv) and imadazole (2.50 g, 1.50 equiv) in dry dimethylformamide (40 ml) was added to a stirred solution of 2,3-O-isopropylidene-D-mannono-1,4-lactone (12) (5.36 g, 24.5 mmol) in dry dimethylformamide (60 ml) at −10° C. under nitrogen. The reaction mixture was then stirred at room temperature for 5 h, when TLC (ethyl acetate:hexane 2:5) showed no starting material ($R_f$ 0.0) and one major product ($R_f$ 0.5). The solvent was removed under reduced pressure and the residue dissolved in chloroform (150 ml); the chloroform solution was washed with water (2×150 ml), dried (magnesium sulphate) and evaporated to give, after purification by flash chromatography (ethyl acetate:hexane, 1:5), 6-O-tert-butyldimethylsilyl-2-3-O-isopropylidene-D-manno-1,4-lactone (13), 7.52 g, 93%), colorless oil, $[\alpha]_D^{20} +51.6°$ (c, 1.33 in $CHCl_3$), $v_{max}$ ($CHCl_3$): 3500 (OH), 1800 (C=O) $cm^{-1}$. (Found: C, 54.20; H, 8.77. $C_{15}H_{28}O_6Si$ requires: C, 54.22; H, 8.43%).

EXAMPLE 4

5-Azido-6-O-tert-butyldimethylsilyl-5-deoxy-2,3-O-isopropylidene-L-gulono-1,4-lactone (15)

A solution of 6-O-tert-butyldimethylsilyl-2,3-O-isopropylidene-D-mannono-1,4-lactone (7.52 g, 22.6 mmol) (13) in dry dichloromethane (100 ml) was cooled to −30° C. under nitrogen and treated with pyridine (3.65 ml, 2.0 equiv) and subsequently with trifluoromethanesulphonic anhydride (5.70 ml, 1.5 equiv). The reaction mixture was stirred at −30° C. for 1 h when TLC (ethyl acetate:hexane, 2:7) showed no starting material ($R_f$ 0.2) and one product ($R_f$ 0.5) and then diluted with chloroform (50 ml), washed with aqueous hydrochloric acid (2M, 100 ml) and water (2×150 ml) and dried (magnesium sulphate); the organic solvents were then removed to give the crude triflate (14) which was used without further purification. The triflate (14) in dry dimethyl formamide (100 ml) was stirred at room temperature with sodium azide (4.41 g, 3.0 equiv) when TLC (ethyl acetate:hexane, 2:7) showed no starting material ($R_f$ 0.5) and only one major product ($R_f$ 0.45). The solvent was removed and the residue partitioned between chloroform (100 ml) and water (100 ml). The chloroform layer was dried (magnesium sulphate) and the solvent removed to give, after purification by flash chromatography (ethyl acetate:hexane, 1:7), 5-azido-6-O-tert-butyldimethylsilyl-5-deoxy-2,3-O-isopropylidene-L-gulono-1,4-lactone (15), (5.66 g, 70%), colorless oil, $[\alpha]_D^{20} +78.5°$ (c, 1.56 in $CHCl_3$), $v_{max}$ ($CHCl_3$); 2100 ($N_3$), 1800 (C=O) $cm^{-1}$; (Found: C, 50.24; H, 7.67; N, 11.48. $C_{15}H_{27}N_3O_5Si$ requires: C, 50.42; H, 7.56; N, 11.76%).

EXAMPLE 5

6-Azido-7-O-tert-butyldimethylsilyl-1,6-dideoxy-3,4-O-isopropylidene-L-gulo-heptul-2-ose (16)

Methyl lithium (1.4M in ether, 8.88 ml, 1.02 equiv) was added to a solution of 5-azido-6-O-tert-butyldimethylsilyl-5-deoxy-2,3-O-isopropylidene-L-gulono-1,4-lactone (15) (4.35 g, 12.2 mmol) in tetrahydrofuran (50 ml) at −78° C. under nitrogen. The reaction mixture was stirred at −78° C. for 15 min when TLC (ethyl acetate:hexane, 1:3) showed no starting material ($R_f$ 0.42) and one major product ($R_f$ 0.54). The reaction mixture was quenched with saturated aqueous ammonium chloride solution (10 ml), diluted with ether (50 ml) and washed with water (2×100 ml); the organic layer was dried (magnesium sulphate) and the solvent removed to give, after purification by flash chromatography (ethyl acetate:hexane, 1:9), 6-azido-7-O-tert-butyldimethylsilyl-1,6-dideoxy-3,4-O-isopropylidene-L-gulo-heptul-2-ose (16), (3.71 g 82%), $v_{max}$ ($CHCl_3$): 3600–3100 (br, OH), 2100 ($N_3$) $cm^{-1}$.

EXAMPLE 6

1,O-tert-Butyldimethylsilyl-4,5-O-isopropylidene-2,6-imino-2,6,7-trideoxy-D-glycero-D-gluco-heptitol (18)

6-Azido-7-O-tert-butyldimethylsilyl-1,6-dideoxy-3,4-O-isopropylidene-L-gulo-heptul-2-ose (16) (3.69 g, 9.89 mmol) in ethyl acetate (60 ml) was stirred in an atmosphere of hydrogen in the presence of a catalyst of platinum(IV) oxide (500 mg) at room temperature for 42 h when TLC (ethyl acetate:hexane, 3:2) showed no starting material ($R_f$ 0.8) and one major product ($R_f$ 0.5). The catalyst was removed by filtration of the reaction mixture through celite and the solvent was removed to give, after purification by flash chromatography (ethyl acetate:hexane, 1:4), 1-O-tert-butyldimethylsilyl-4,5-O-isopropylidene-2,6-imino-2,6,7-trideoxy-D-glycero-D-gluco-heptitol (18), (1.53 g, 47%), m.p. 98°–99° C., $[\alpha]_D^{20} +40.7°$ (c, 1.17 in $CHCl_3$), $v_{max}$ ($CHCl_3$); 3600–3300 (br, OH) $cm^{-1}$; (Found: C, 57.90; H, 10.34; N, 3.98. $C_{16}H_{33}NO_4Si$ requires: C, 58.01; H, 9.97; N, 4.23%).

EXAMPLE 7

2,6-Imino-2,6,7-trideoxy-D-glycero-D-gluco-heptitol (6)

1-O-tert-Butyldimethylsilyl-4,5-O-isopropylidene-2,6-imino-2,6,7-trideoxy-D-glycero-D-glucoheptitol (18) (420 mg, 1.27 mmol) in 50% aqueous trifluoroacetic acid (20 ml) was stirred at room temperature for 5 h and the reaction mixture was evaporated to dryness; the residue was washed with chloroform (2×20 ml) to give the trifluoroacetate salt of (6). Purification by ion exchange chromatography (Sigma CG-400 OH⁻ form, then Aldrich 50x, 8-100, H⁺ form, eluted with 0.5M aqueous ammonium hydroxide) gave the hygroscopic free base, 2,6-imino-2,6,7-trideoxy-D-glycero-D-gluco-heptitol (6), (223 mg, 100%), m.p. 61°–64° C., $[\alpha]_D^{20} +40.3°$ (c, 0.90 in $H_2O$), $v_{max}$ (KBr) 3700–3000 (br, OH and NH) $cm^{-1}$; (Found: C, 47.30; H, 8.45; N, 7.70. $C_7H_{15}NO_4$ requires: C, 47.46; H, 8.47; N, 7.91%). The free base (6) (100 mg, 0.56 mmol) was dissolved in water (3 ml) and the solution adjusted to pH 4 with dilute aqueous hydrochloric acid; the reaction mixture was freeze dried to give, after recrystallization from ethanol:ethyl acetate (1:1), the hydrochloride of (6), (119 mg, 99%), m.p. 190°–192° C., suitable for X-ray crystallographic analysis.

X-Ray Crystal Structure Analysis. The structure of the hydrochloride of 2,6-imino-2,6,7-trideoxy-D-glycero-D-gluco-heptitol (6), including the absolute configuration, was established by single crystal x-ray analysis.

EXAMPLE 8

Inhibition of a-L-fucosidase by 2,6-imino-2,6,7-trideoxy-D-glycero-D-gluco heptitol (6) was demonstrated as follows:

Materials and Methods

Tissue Post-mortem human liver, which had been stored at $-20°$ C. until required was homogenized in deionized water (50%, w/v) in a Potter-Elvehjem homogenizer and then centrifuged at 37,000 g for 30 min in an MSE 18 centrifuge. The resultant supernatant was used as the source of human glycosidases. A lyophilized extract of liver from Charonia lampas was obtained from Seikagaku Kogyo Co., Japan for the isolation of α-L-fucosidase by the published procedure of Iijima and Egami, *J. Biochem.* 70, 75–78 (1971).

Enzyme Assays The glycosidase activities in an extract of human liver were assayed by using the appropriate fluorigenic 4-umbelliferyl glycoside substrate (Koch-Light, Haverhill, Suffolk, U.K.) with a concentration of 0.5 mM at the optimal pH for each enzyme [Burditt et al., *Biochem. J.* 189, 467–473 (1980)]. The specificity of the inhibitors was determined by assaying the glycosidases in the presence of and absence of a 1 mM solution of each compound. The nature of the inhibition of human α-L-fucosidase, the value of Ki determined by using the Dixon graphical procedure and the effect of pH on the inhibition were investigated as described previously by Al Daher et al., *Biochem. J.* 258, 613–615 (1989). Bovine epididymal and Charonia lampas α-L-fucosidase were assayed using para-nitrophenyl α-L-fucopyranoside as substrate in phosphate-citrate buffer (McIlvaine), pH 6.0, and 0.05M-sodium acetate buffer, pH 4.5 containing 0.15M NaCl, respectively. The Lineweaver-Burk graphical procedure and secondary plots of the slope against inhibitor concentration were used to determine the nature of inhibition and the values of Ki for these activities.

The inhibitory results were as follows:

TABLE 1

| Compound | pKa | Inhibition of α-L-fucosidase $K_i$(M) | Other specificities (% inhibition at 1 mM) |
|---|---|---|---|
| (6) | 7.7 | $5 \times 10^{-6}$ | β-D-glucuronidase |
| DFJ | 8.4 | $1 \times 10^{-8}$ | N-acetyl-β-D-hexosaminidase (59%) |

DFJ = deoxyfuconojirimycin

Various other examples will be apparent to the person skilled in the art after reading the present disclosure without departing from the spirit and scope of the invention. It is intended that all such other examples be included within the scope of the appended claims.

We claim:

1. A method for the production of 2,6-imino-2,6,7-trideoxy-D-glycero-D-gluco-heptitol comprising catalytically hydrogenating 6-azido-7-O-tert-butyldimethylsilyl-1,6-dideoxy-3,4-O-isopropylidene-L-gulo-heptulo-2-ose with platinum (IV) oxide at about room temperature followed by hydrolytic removal of the silyl and isopropylidene protecting groups.

2. The method of claim 1 in which the catalytic hydrogenation is conducted in ethyl acetate solvent in the presence of platinum (IV) oxide catalyst.

* * * * *

UNITED STATES PATENT AND TRADEMARK OFFICE
CERTIFICATE OF CORRECTION

PATENT NO. : 5,153,325

DATED : Oct. 6, 1992

INVENTOR(S) : George W. J. Fleet and Sung K. Namgoong

It is certified that error appears in the above-identified patent and that said Letters Patent is hereby corrected as shown below:

On the title page, under Related U.S. Application Data, "Pat. No. 4,849,430" should read --Pat. No. 5,017,704--;

In col. 1, line 7, "U.S. Pat. No. 4,849,430" should read --U.S. Pat. No. 5,017,704--. In col. 1, line 26, after "Sep. 23, 1988" insert --,now U.S. Pat. No. 4,849,430,--.

Signed and Sealed this

Twenty-first Day of December, 1993

Attest:

BRUCE LEHMAN

Attesting Officer

Commissioner of Patents and Trademarks